United States Patent
Neuss

(10) Patent No.: US 10,874,534 B2
(45) Date of Patent: Dec. 29, 2020

(54) DOUBLE STENT

(71) Applicant: MOB.Ing GmbH, Loerrach (DE)

(72) Inventor: Malte Neuss, Bonn (DE)

(73) Assignee: MOB.ING GMBH, Loerrach (DE)

( * ) Notice: Subject to any disclaimer, the term of this patent is extended or adjusted under 35 U.S.C. 154(b) by 41 days.

(21) Appl. No.: 16/344,902

(22) PCT Filed: Oct. 26, 2017

(86) PCT No.: PCT/EP2017/077454
§ 371 (c)(1),
(2) Date: Apr. 25, 2019

(87) PCT Pub. No.: WO2018/078019
PCT Pub. Date: May 3, 2018

(65) Prior Publication Data
US 2019/0262150 A1 Aug. 29, 2019

(30) Foreign Application Priority Data
Oct. 26, 2016 (DE) .................. 10 2016 120 445

(51) Int. Cl.
*A61F 2/915* (2013.01)
*A61F 2/07* (2013.01)
(Continued)

(52) U.S. Cl.
CPC ............ *A61F 2/852* (2013.01); *A61F 2/07* (2013.01); *A61F 2/844* (2013.01); *A61F 2/915* (2013.01); *A61F 2002/0072* (2013.01); *A61F 2002/828* (2013.01); *A61F 2002/91516* (2013.01); *A61F 2002/91533* (2013.01); *A61F 2002/91583* (2013.01); *A61F 2210/0014* (2013.01); *A61F 2210/0076* (2013.01); *A61F 2220/0033* (2013.01); *A61F 2220/0091* (2013.01)

(58) Field of Classification Search
CPC ....... A61F 2/07; A61F 2002/072; A61F 2/852
See application file for complete search history.

(56) References Cited

U.S. PATENT DOCUMENTS 5,667,253 A * 9/1997 Jansen ................... B67D 7/344
285/26
5,916,264 A 6/1999 Von Oepen et al.
(Continued)

FOREIGN PATENT DOCUMENTS

DE 197 20 115 A1 12/1998
DE 296 23 983 U1 12/2000
WO 2012/084202 A2 6/2012

OTHER PUBLICATIONS

International Search Report in PCT/EP2017/077454, dated Feb. 2, 2018.

*Primary Examiner* — Suba Ganesan
(74) *Attorney, Agent, or Firm* — Collard & Roe, P.C.

(57) ABSTRACT

The invention relates to a double stent comprising coaxially arranged stents, wherein a first membrane (4) being arranged between a first inner stent (2) and at least two outer stents (3), and a second membrane (5) being arranged on the outer stents (3), with the membrane ends of the first (4) and second membrane (5) being brought together at the ends of the stents (2, 3) and folded around to the inside of the first stent (2) and clamped securely under flexible tongues (6) of the first stent (2).

13 Claims, 2 Drawing Sheets

(51) Int. Cl.
    *A61F 2/852*     (2013.01)
    *A61F 2/844*     (2013.01)
    *A61F 2/82*     (2013.01)
    *A61F 2/00*     (2006.01)

(56) References Cited

U.S. PATENT DOCUMENTS

| | | |
|---|---|---|
| 8,888,837 B2 | 11/2014 | Obradović et al. |
| 2005/0209679 A1* | 9/2005 | Melsheimer .............. A61F 2/07 623/1.15 |

* cited by examiner

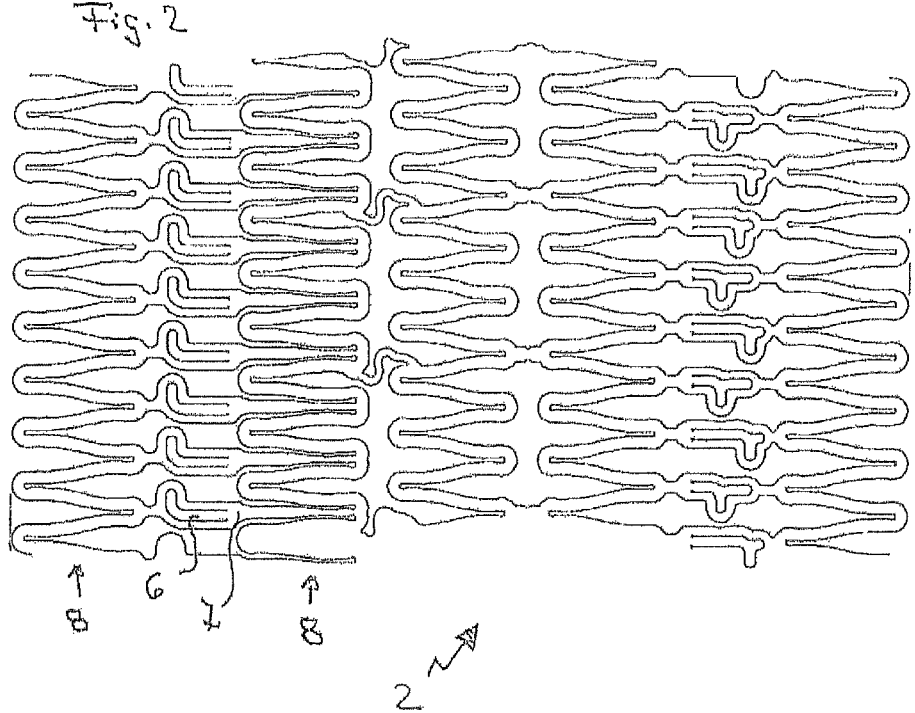
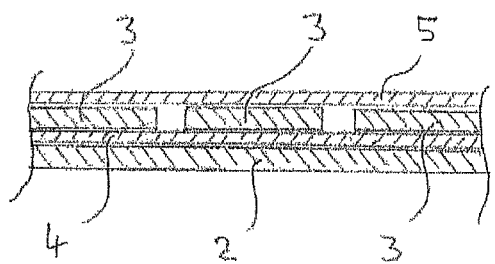

DOUBLE STENT

CROSS REFERENCE TO RELATED APPLICATIONS

This application is the National Stage of PCT/EP2017/077454 filed on Oct. 26, 2017, which claims priority under 35 U.S.C. § 119 of German Application No. 10 2016 120 445.5 filed on Oct. 26, 2016, the disclosure of which is incorporated by reference. The international application under PCT article 21(2) was not published in English.

The invention relates to a double stent comprising coaxially arranged stents, whereby a first membrane is arranged between a first inner stent and at least two outer stents. The double stent is used in particular as a stent graft for the purpose of bridging vascular malformations, such as aneurysms and shunts, but also to reinforce unstable, fragile or thrombotic vessel walls. It is, moreover, applied as a bridging element for branches leading out of stented vessels.

Stent grafts for bridging vascular malformations are known in a variety of forms. As a rule, they consist of a stent that is completely or partially covered with a membrane. The membrane occludes the vascular malformation against the vessel, the stent keeps the vessel open and ensures that the membrane is in close contact with the vessel wall.

One problem with stent grafts concerns the anchoring of the membrane to the stent. Double stents were developed for this purpose, in which the membrane is held between an outer and an inner stent. During the expansion of such a double stent, the membrane participates in the radial expansion but remains clamped between the two stents.

Such a double stent is known, for example, from what has been disclosed in DE 197 20 115 A1. The stent described there has proven its worth in and of itself, but can be improved in two respects.

On the one hand, problems with tightness are often encountered, as the membrane is not in close contact with the vessel wall and/or is damaged during the expansion of the double stent. In both cases, the double stent does not meet the requirements placed on it, namely the occlusion of, for example, a vascular malformation.

On the other hand, the expansion of the double stent may cause the composite of two stents and a membrane to lose coherence, for example if the two stents exhibit a different expansion behavior—for example due to local conditions.

What is more, the maneuverability of such double stents deteriorates. Two stents of the same length arranged one above the other lead to stiffening, which—especially in the case of longer stents—leads to problems during passage through and placement in tortuous vessels.

When normal stent grafts are used, the radial force of a single stent, whether of balloon expandable or self-expanding type, is not sufficient in many cases to securely anchor the membrane and/or ensure a reliable and permanent bridging or expansion of the vessel. In these cases, the use of a double stent with increased radial force is considered expedient This applies in particular to self-expanding stents, which generally exhibit a lower radial force than balloon-expandable stents.

It is, therefore, the objective of the invention to provide a double stent that meets the requirements with respect to tightness and reliability on the one hand and, moreover, warrants the required coherence on the other. In addition, the stent should possess high radial force and good flexibility.

This objective is achieved with a double stent of the kind first mentioned above, in which a second membrane is arranged on the outer stents, wherein the membrane ends of the first and second membrane being brought together at the ends of the stents, folded over to the inside of the first stent and clamped under flexible tongues of the first stent.

The double stent proposed by the invention not only comprises an inner and at least two outer stents but is also provided with an inner and outer membrane. What is more, the inner and outer stents complement each other in terms of radial force and the two membranes in terms of tightness. The outer second membrane serves as protection and supplement to the inner first membrane so that, if the inner membrane is damaged during expansion, for example tears, the outer membrane is capable of compensating for this defect and vice versa. Furthermore, the outer membrane holds the construct together, and anchoring the ends of the outer membrane together with the ends of the inner membrane on the inside of the inner stent contributes to the coherence of the elements.

For the stents used according to the invention, the usual stent designs, such as those often developed for balloon-expandable and self-expanding stents, can be put to use. For balloon-expandable stents any materials customary for this purpose may be employed, for example, steel alloys for medical use, cobalt-chromium alloys and the like. As regards self-expanding stents, materials with shape memory properties are particularly suitable, such as nickel-titanium alloys. Combinations of stents made of these materials can also be used. Moreover, stents or individual stents can be made of plastic. A combination of plastic and metal stents is also possible, whereby the inner stent preferably consists of plastic.

A combination of an inner stent made of nitinol or another shape memory alloy and one or more outer stents made of a cobalt-chromium alloy is particularly preferred. This combination offers advantages with respect to placement by means of a balloon catheter, in terms of radial force provided essentially by the outer stents, and in terms of keeping the vessel open by the inner stent.

The stents can be braided, but are usually cut from a tube of suitable diameter using a laser cutting technique. They feature a mesh structure.

For example, the stents may have a mesh structure as formed by intersecting webs. Stents consisting of a plurality of meandering ring segments are preferred, with said ring segments being connected to adjacent ring segments by means of connecting webs. In this case, too, meshes are produced, the size of which is determined by the frequency of the connecting webs existing between two adjacent ring segments. Such a stent structure is suited to at least partially compensate for the length reduction that occurs during expansion depending on the arrangement and shape of the connecting webs.

The flexible tongues located on the inner first stent can have a variety of shapes. In particular, the flexible tongues point into a direction outwards of the stent, i.e. they point to the edge of the stent. Such flexible tongues are arranged in particular on connecting webs of the ring segments, the film ends being clamped and secured between the connecting webs and the flexible tongues originating from the connecting webs.

Preferably, the flexible tongues are cut into the connecting webs, i.e. to be movable with respect to the connecting webs. It is also preferred to locate the flexible tongues on connecting webs located at the periphery of the inner stent, such as connecting the first peripheral ring segment to the second adjacent one.

Clamping the membrane ends on the inside of the inner stent results in reliably anchoring and securing the two membranes and strengthens the bond comprising inner stent, inner membrane, outer stent and outer membrane.

Any biological or artificial material suitable for the purpose can be employed for the membranes. Usually, the membranes consist of plastic material, preferably a plastic tube, which is pulled over the respective stent. For example, a suitable material is polytetrafluoroethylene, PTFE, especially ePTFE, which has the elasticity required for the expansion process. Other plastics unobjectionable from a medical viewpoint, such as polyester, polyolefins, polyurethanes, polyurethane carbonate and the like, may also be employed.

The inner stent and the outer stents—taken together—of the double stent proposed by the invention preferably have the same length and 100% overlap. However, they can also be offset from each other—partial overlap—or have different lengths. These variants lead to a stiffening of the overlap area and to an increased flexibility in areas without overlapping, which results in a good adaptability and also ensures that a secure fit is achieved.

The double stent principle involving two membranes naturally leads to a relatively high wall thickness of the construct, which restricts maneuverability in the vascular system of a patient. This can be counteracted by selecting a low wall thickness of the tubes from which the stents are cut, for example in the range of between 0.05 and 0.50 mm, preferably between 0.10 and 0.20 mm and in particular approx. 0.15 mm. The web width can be reduced as well, for example, to between 0.05 and 0.50 mm, preferably between 0.10 and 0.20 mm and in particular approx. 0.15 mm. As a result of two stents being used, it is still ensured that a high radial force is achieved.

It is preferred, moreover, to provide the outer stents with meshes that are smaller than those of the inner stent. In this way, a compressive stress is created during expansion, which has an advantageous effect on the radial force and the coherence of the construct. This ensures that high strength and durability of the construct are achieved.

It is to be understood that customary methods are used for the placement of the double stent in the target vessel, usually a balloon catheter onto which the double stent is crimped.

The inventive double stent is particularly suitable for placement in branches of stented vessels and thus for bridging the space that forms between the stented vessel and the branch.

Within the double stents provided by the invention two or more outer stents can be arranged, each of which performing a supporting function. Aside from the two stents, which are arranged at the ends of the stent for example, a third stent may also be arranged in the middle. Essential in this context is that the outer stents are movable against each other so that the double stent has increased flexibility in these areas where there is no overlap or where the outer stents abut each other. In addition to achieving excellent maneuverability also in convoluted vessels, this also enables the supporting function to adapt to the respective conditions of a vessel.

It shall furthermore be understood that the thickness (wall thickness) of the outer stents may differ from that of the inner stent. In this case, the wall thickness of the inner stent usually is greater than that of the outer stents.

The outer stents as well may vary in thickness to satisfy the requirements with respect to flexibility and radial force.

As a rule, the outer stents arranged one after the other are not connected to each other. However, a loose connection may also be provided, for example via adhesive points or welding points, articulated connections or a cardanic connection. Articulated elements are known for the joining of stents. A cardanic connection is created, for example, by connecting two stents by means of two connecting webs which can face each other and which are preferably of curved or s-shaped configuration.

The stents can be made of customarily known materials, for example of medical steel, cobalt-chromium alloys and nickel-titanium alloys or optional combinations thereof. Plastics, for example resorbable plastic materials, as they are known from the state of the art, may also be employed, as well as combinations consisting of metal stents and plastic stents, for example in the form of an inner stent of metal and several outer stents made of plastic material.

The combination of an inner and several outer stents provided with an intermediate membrane and a covering membrane fixed to the inner side of the inner stent results in an extremely stable implant that still offers a high degree of flexibility. The two membranes contribute to stabilization and allow the stent walls to be kept very thin. Nevertheless, the stent exhibits good radial force.

The outer stents can be arranged as required for the respective application purpose. To achieve an improved supporting function in the end areas, it is sufficient to have only these areas overlap. Should a reinforcement be required over the entire length, the outer stent layer may consist of a number of individual stents which may be insulated or connected with each other as described above.

Further elucidation of the invention is provided through the enclosed figures showing preferred embodiments of the invention. It goes without saying that the characteristics shown in the figures shall in each case be regarded individually as being part of the invention and should not be understood exclusively in the context of the other characteristics illustrated in the figures, where FIG. 1 is a schematic representation of a stent in accordance with the invention;

FIG. 2 shows a variant of the clamping principle used for the membranes; and

FIG. 3 illustrates a section through the wall of a stent proposed by the invention.

Figure 1:
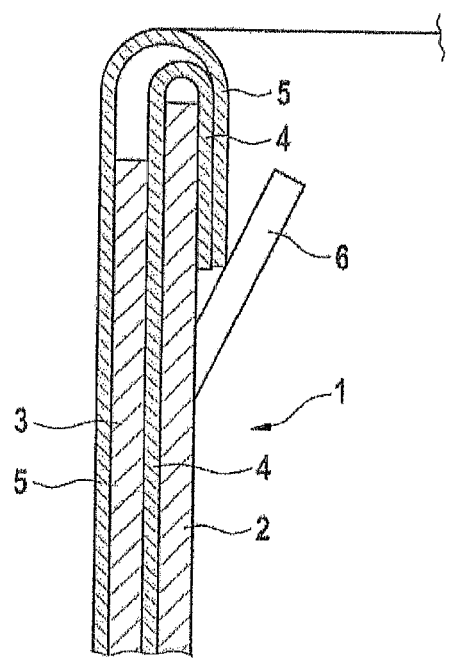

The double stent 1 shown in FIG. 1 comprises a first inner stent 2 and a second outer stent 3 that are arranged coaxially to each other. The outer stent 3 is slightly shorter than the inner stent 2. The double stent is shown in the non-expanded state. Between the inner stent 2 and the outer stent 3 a first inner membrane 4 is provided and on the outer stent 3 a second outer membrane 5 is arranged, with both membranes being made of ePTFE.

The inner membrane 4 and the outer membrane 5 are brought together at their ends and folded inwards into the cavity of the inner stent 2 around the edge of the two stents. Schematically shown in the figure is one of several flexible tongues 6, which is bent inwards and under which the membrane ends protrude. For the purpose of fixing the membrane ends, the flexible tongues 6 are bent back outwards resulting in the membrane ends being clamped underneath them.

In FIG. 2 a stent design is illustrated for the inner stent 2, said design providing for two closely to the periphery adjacently arranged ring segments 8 to be joined together by means of connecting webs 7. Flexible tongues 6, which are movable with respect to the stent plane, are cut into the connecting webs 7.

With a view to increasing the contact area for the tubular film (not shown), the flexible tongues 7 are of angled configuration in the free end area which improves the clamping effect in relation to the inserted membrane.

FIG. 3 illustrates the principle of the double stent proposed by the invention comprising a single inner stent 2, two terminally located stents 3 and stent 3 in the middle position, as well as the intermediate membrane 4 and the covering membrane 5, both folded around inwards.

The invention claimed is:

1. A double stent comprising coaxially arranged stents, wherein a first membrane is arranged between a first inner stent and at least two outer stents, wherein a second membrane is arranged on the at least two outer stents and
wherein the membrane ends of the first membrane and the second membrane are brought together at the ends of the first inner stent and the at least two outer stents and are folded over onto the inside of the first inner stent and clamped securely under flexible tongues of the first inner stent.

2. The double stent according to claim 1, wherein at least one of the first inner stent and the at least two outer stents has a mesh structure.

3. The double stent according to claim 1, wherein at least the first inner stent is provided with a plurality of ring segments arranged side by side and having a meandering structure which are connected to one another by means of webs.

4. The double stent according to claim 3, wherein the flexible tongues are provided at connecting webs between adjacently arranged ring segments of the first inner stent (2).

5. The double stent according to claim 4, wherein the flexible tongues are cut into the connecting webs.

6. The double stent according to claim 1, wherein the flexible tongues point to the outside of the first inner stent.

7. The double stent according to claim 1, wherein the flexible tongues are arranged in the peripheral end regions of the first inner stent.

8. The double stent according to claim 1, wherein the at least two outer stents are arranged at the ends of the double stent.

9. The double stent according to claim 1, wherein the at least two outer stents are flexibly connected with each other.

10. The double stent according to claim 9, wherein the first membrane and/or the second membrane comprises ePTFE.

11. The double stent according to claim 1, wherein each of the at least two outer stents has a structure that is denser than that of the first inner stent.

12. The double stent according to claim 1, wherein each of the first inner stent and the at least two outer stents have webs arranged with gaps between the webs.

13. The double stent according to claim 1, wherein the first membrane and/or the second membrane comprises plastic material.

* * * * *